United States Patent [19]

Comeaux

[11] Patent Number: 5,151,030
[45] Date of Patent: Sep. 29, 1992

[54] DENTAL FILLER APPLICATOR

[76] Inventor: Robert I. Comeaux, 12666 Brookshire Ave., Baton Rouge, La. 70815

[21] Appl. No.: 729,485

[22] Filed: Jul. 12, 1991

[51] Int. Cl.⁵ .............................................. A61C 1/07
[52] U.S. Cl. .................................. 433/118; 433/122; 433/164
[58] Field of Search ................. 433/86, 103, 118, 119, 433/122, 125, 164, 120, 217.1, 226, 83, 89, 121, 123, 124; 128/62 A

[56] References Cited

U.S. PATENT DOCUMENTS

| | | | |
|---|---|---|---|
| 823,150 | 6/1906 | Alexander | 433/122 |
| 2,911,660 | 11/1959 | Klemas et al. | 128/62 A |
| 3,183,538 | 5/1965 | Hubner | 128/62 A |
| 3,280,459 | 6/1963 | Walker et al. | 32/60 |
| 3,890,713 | 6/1975 | Nielsen | 32/60 |
| 3,965,578 | 6/1976 | Warden et al. | 32/60 |
| 3,967,617 | 7/1976 | Krolik | 128/62 A |
| 4,092,778 | 6/1978 | Hirdes | 32/60 |
| 4,333,197 | 6/1982 | Kuris | 433/119 |
| 4,820,152 | 4/1989 | Warrin | 433/86 |
| 4,997,371 | 3/1991 | Fischer | 433/90 |
| 5,000,684 | 3/1991 | Odrich | 433/118 |
| 5,002,487 | 3/1991 | Tichy | 433/118 |

FOREIGN PATENT DOCUMENTS 3409543 9/1985 Fed. Rep. of Germany ...... 433/119

Primary Examiner—Cary E. O'Connor
Attorney, Agent, or Firm—David L. Ray

[57] ABSTRACT

In accordance with the present invention there is provided a tool for applying a filling material to a tooth cavity or other surface including a housing for grasping by the hand of the user, a vibrator contained within the housing for vibrating the housing, a brush for applying or shaping and molding cavity filler material, and an elongated brush holder connected to the housing and to the brush.

13 Claims, 1 Drawing Sheet

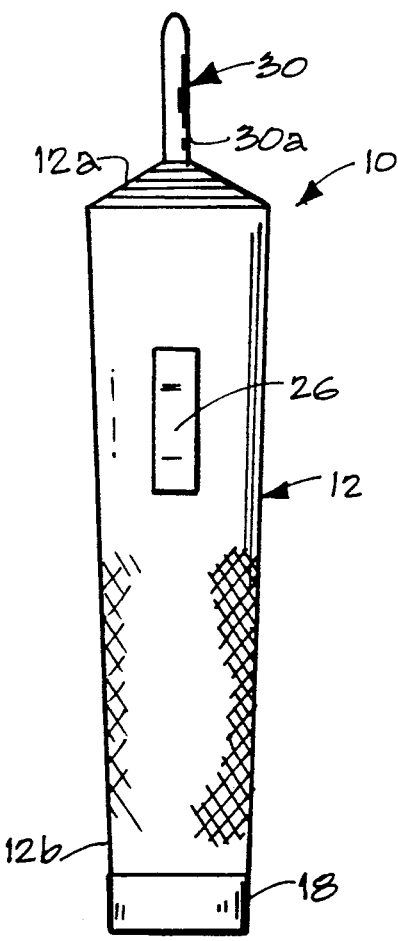
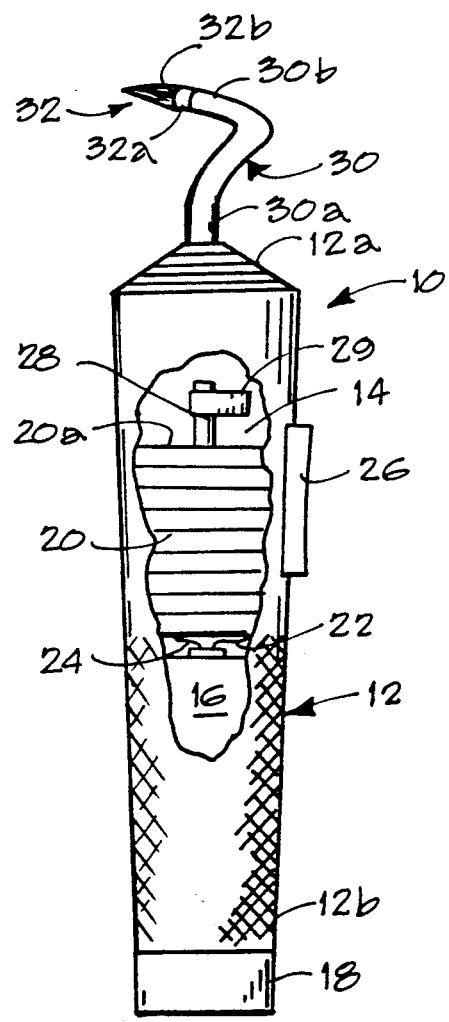
FIGURE 1
FIGURE 2

DENTAL FILLER APPLICATOR

BACKGROUND OF THE INVENTION

1. Field of the Invention

The invention relates to tools used by a dentist. In particular, the present invention relates to tools for applying a filling material to a cavity in a tooth.

2. Description of the Related Art

Dental tools and appliances are well known in the art. Exemplary of some of the dental tools and appliances and tools of the prior art are the following U.S. patents:

U.S. Pat. No. 4,820,152 discloses a single multi-function handpiece for dental instruments that can be used in multiple dental treatments. The handpiece comprises a housing having a coil for producing an electromagnetic or electrostrictive field in the housing, and a number of inserts that react with the electromagnetic or electrostrictive field and can be used with the housing to complete the handpiece. A switching system used with the handpiece, which electrically recognizes the particular insert used with the housing provide for automatically controlling circuitry that determines which of a number of materials and medicaments are to be delivered to the handpiece for use with a particular insert. Circuitry which provides better control of the ultrasonic insert in the handpiece is also provided.

U.S. Pat. No. 4,092,778 discloses a discloses a dental appliance for introducing a filler material into a tooth cavity that has a support which carries a discharge nipple having an elongated interior channel formed with an inlet and an outlet. A pair of tubular guides form a first and a second passage, respectively. The first passage has an open end and the second passage communicates with the inlet of the interior channel. A replacable magazine has an elongated chamber for a quantity of the filler material and communicates of the open end of the channel in direction transversely to the elongation of the latter. A first expelling element is reciprocable in the first passage and the chamber for expelling a portion of the chamber material and charging it into the channel. A second expelling element is reciprocable in the second passage and channel for expelling the charged portion through the outlet of the nipple. A single drive is provided which effects coordinated reciprocation of both of the expelling elements.

U.S. Pat. No. 3,965,578 discloses a combined amalgam carrier and dental handpiece comprising a power source, a plugger, and a disposable cartridge assembly removably engageable with the power source, the plugger being carried by the power source and selectively movable with respect to the cartridge for passing therethrough in a reciprocal movement, the cartridge including a housing preloaded with selected quantities of mercury and silver, or the like, in separated sealed compartments, and a device extending through the housing and engagable with the power source for longitudinal and rotatable movement with respect to the housing, the longitudinal movement causing a combining of the initially separated mercury and silver components, the rotatable movement causing both mixing of the components to produce amalgam for denture fillings and discharging of said amalgam from the housing for engagement thereof by the plugger, and the plugger being selectively reciprocal through the cartridge for implanting multiple charges of the amalgam in a tooth cavity, or the like, and packing the charges in the cavity.

U.S. Pat. No. 3,890,713 discloses a dental implement for use in connection with filling of tooth cavities with amalgam or a similar tooth filling material, characterized in that it is made as a hand tool having a narrow outlet spout for amalgam and an amalgam container communicating with the spout for dispensing amalgam therethrough, and a vibrator unit serving to vibrate a tool part by means of which the amalgam in the cavity can be compressed or condensed. In the outlet spout there is mounted a plunger or hammer element connected to a vibrator and serving to push the filling material into the tooth cavity in a beat like manner with a relatively high working frequency, e.g. 500 cycles per minute, whereby it is possible to rapidly fill the cavity with many small portions of the filling material and with positive compression or condensation of each of these portions. The advantage of using the device is not only a considerable saving of work but also that in practice it becomes possible to fill the tooth cavity according to the so-called "wet" method whereby filling of a highly improved quality is obtainable.

U.S. Pat. No. 3,280,459 discloses a combined amalgamator and dispenser device for storing, mixing, and dispensing having an elongated passage, a piston movable within the passage for displacing and mixing ingredients therein, a movably mounted gate for blocking movement of the ingredients through passage means, storage, a device for transferring measured amounts of the ingredients from the storage device to the passage, and a device for sequentially imparting axial movement and rotation to the piston when the passage means is blocked by the gate to receive and mix the ingredients in the passage, and a device operative on the gate to unblock the passage and cause resumption of axial movement of the piston means through the gate for dispensing the mixed ingredients.

SUMMARY OF THE INVENTION

In accordance with the present invention there is provided a dental tool for applying a filling material to a tooth cavity, or shaping and molding a filling material which has been applied to a tooth cavity, including a housing for grasping by the hand of the user, a vibrator contained within the housing for vibrating the housing, a brush for applying or for shaping and molding cavity filling material, and an elongated brush holder connected to the housing and to the brush.

The tool of the invention enables filling material to be quickly and accurately applied to a cavity.

The tool of the invention enables filling material which has been applied to a tooth cavity to be quickly and easily shaped and molded to the desired configuration.

The dental tool of the invention has the advantage of being low in cost.

Furthermore, the dental tool of the invention is easy to operate.

BRIEF DESCRIPTION OF THE DRAWINGS

FIG. 1 is an elevational view of the dental tool of the invention; and

FIG. 2 is a partly cut-away, schematic, elevational view of the dental gun of the invention rotated 90 degrees counter-clockwise from the view shown in FIG. 1.

BRIEF DESCRIPTION OF THE PREFERRED EMBODIMENTS

Referring now to the drawings, in FIGS. 1 and 2 is shown the dental tool of the invention generally indicated by the numeral 10. The dental tool 10 has a housing generally indicated by the numeral 12 which is generally cylindrical in shape and is hollow inside. Housing 12 has an top end 12a and a bottom end 12b. The hollow interior of housing 12 is indicated by the numeral 14.

Located in the hollow interior 14 of housing 12 is battery 16. Battery 16 may be rigidly connected to the hollow interior 14 of housing 12 by in any conventional manner known in the art. Battery 16 may be any conventional direct current storage battery well known in the art. Such batteries are commonly available and are sometimes referred to as flashlight batteries. Battery 16 may be rechargeable or non-rechargeable.

A removable plug 18 is located in the bottom end 12b of housing 12 to permit battery 16 to be changed when it is discharged. Plug 18 may be fitted into the bottom end 12b of housing 12 in any conventional manner known in the art such as force-fitting or threading.

Also located in the interior 14 of housing 12 is electric motor 20. Electric motor 20 is rigidly connected to the interior 14 of housing 12 in any conventional manner. Electric motor 20 may any conventional electric motor well known in the art. Preferably, electric motor 20 is a direct current electric motor capable of being energized and driven by battery 16.

Electric motor 20 is electrically connected to motor 20 by electrically conductive wires 22 and 24. A conventional switch 26 is electrically connected to motor 20 to start or stop motor 20. Switch 26 may be electrically connected to motor 20 in any conventional manner known in the art. Switch 26 is preferably a slide switch which slides toward the top end 12a or bottom end 12b of housing 12 to energize or de-energized motor 20.

Connected to the top end 20a of motor 20 is rotatable shaft 28. Rotatable shaft 28 is rotated when motor 20 is energized.

Rigidly connected to rotatable shaft 28 is weight 29. As can be seen in FIG. 2, weight 29 extends to one side of rotatable shaft 28. Thus, when rotatable shaft 28 is rotating, motor 20 and housing 12 vibrate due to the rotation of off-center weight 29.

Rigidly connected to the top end 12a of housing 12 is elongated brush holder generally indicated by the numeral 30. Brush holder 30 has a generally vertical base portion 30a connected to housing 12, and a curved, generally horizontal upper portion 30b. Brush holder 30 may be shaped as desired.

Upper portion 30b has a brush generally indicated by the numeral 32 rigidly connected thereto. Brush 32 preferably has a rigid base 32a which may removably connected to upper portion 30b in any manner well known in the are such as force-fitting, threading, or the like.

Brush 32 has fibers 32b connected to base 32a. Fibers 32b are preferably sable hair, although synthetic fibers such as hair-like plastic filaments may be used if desired. Any hair-like fiber which will hold cavity filling material and release the material to the surface of the tooth cavity to be filled may be used. Furthermore, fibers 32b which will not hold the cavity filling material may also be used to shape and mold cavity filling material which has been applied to the cavity by a syringe or other suitable instrument known to those skilled in the art.

To use the dental tool of the invention with fibers 32b which will hold the cavity filling material, the housing is grasped by the hand of the user and the fibers 32b are forced against cavity filling material(not shown) contained in a reservoir or container until the desired amount of cavity filling material is carried on the fibers 32b. The motor 20 may be energized or de-energized when the fibers 32b are forced against the filling material.

After the fibers 32b are loaded with cavity filling material(not shown), the motor 20 is energized to vibrate the housing 12, brush holder 30, base 32a, and fibers 32b. The fibers 32b are then forced against the cavity(not shown) to deposit cavity filling material in the cavity. The vibrating fibers 32b enable the cavity filling material to be quickly and accurately placed in the cavity.

To use the dental tool of the invention with fibers 32b which will not hold the cavity filling material, the housing is grasped by the hand of the user and the fibers 32b are forced against cavity filling material(not shown) previously applied to the tooth cavity by a syringe or other instrument known to those skilled in the art. The motor 20 is energized and the fibers 32b are forced against the filling material to spread and shape the cavity filling material to the desired configuration. The vibrating fibers 32b enable the cavity filling material to be quickly and easily shaped and molded in the tooth cavity.

The tool of the invention may also be used in other applications other than dental work. The tool of the invention may be used to apply any desired filling material or other material to a desired surface.

Although the preferred embodiments of the invention have been described in detail above, it should be understood that the invention is in no sense limited thereby, and its scope is to be determined by that of the following claims:

What is claimed is:

1. A tool for causing a filling material to fill a cavity of a tooth comprising:
   a. hollow housing means for grasping by the hand of the user, said housing means having a top end and a bottom end,
   b. vibrator means located in said housing means for vibrating said housing means,
   c. a single brush for molding and shaping a filling material, the brush having a fiber tip connected to a rigid base, said fiber tip being adapted to hold filling material thereon, said fiber tip being sable hair, and
   d. brush holder means connected to said top end of said housing means and to said brush for holding said rigid base of aid brush.

2. The dental tool of claim 1 wherein said bottom end of said housing means has removable plug means therein.

3. The dental tool of claim 1 wherein said vibrator means includes electric motor for causing said housing means to vibrate.

4. The dental tool of claim 3 wherein said motor has a rotatable shaft rotated by said motor, said rotatable shaft having weight means connected thereto, said weight means being connected to one side of said rotatable shaft.

5. The dental tool of claim 4 wherein battery means are located in said housing means to energize said motor means.

6. A method for applying a filling material to a tooth cavity comprising:
   a. placing filling material on a brush,
   b. placing said brush on the cavity to be filled, and
   c. vibrating the brush to transfer the filling material into said cavity.

7. The method of claim 6 wherein said vibrating is caused by motor means connected to said brush.

8. The method of claim 7 wherein said motor means is an electric motor.

9. The method of claim 8 wherein said vibrating is caused by a rotatable shaft driven by said motor.

10. The method of claim 8 wherein said vibrating is caused by a rotatable shaft driven by said motor.

11. The method of claim 7 wherein said motor means is an electric motor.

12. The method of claim 6 wherein said vibrating is caused by motor means connected to said brush.

13. A method for applying a filling material to a tooth cavity comprising:
    a. placing filling material on a tooth having a cavity,
    b. placing a brush on the cavity to be filled, and
    c. vibrating the brush to transfer the filling material into said cavity.

* * * * *